(12) United States Patent
Kobayashi et al.

(10) Patent No.: US 6,190,519 B1
(45) Date of Patent: Feb. 20, 2001

(54) GAS SENSOR ELEMENT

(75) Inventors: Shigeyoshi Kobayashi; Zhang Yi Can, both of Saitama; Shigeyuki Kimura, Gunma, all of (JP)

(73) Assignees: Akebono Brake Industry Co., Ltd., Tokyo; Akebono Research and Development Center Ltd., Saitama, both of (JP)

( * ) Notice: Under 35 U.S.C. 154(b), the term of this patent shall be extended for 0 days.

(21) Appl. No.: 09/277,190

(22) Filed: Mar. 26, 1999

(30) Foreign Application Priority Data

Mar. 27, 1998 (JP) .................................................. 10-080684

(51) Int. Cl.[7] .............................................. G01N 27/407
(52) U.S. Cl. ........................................ 204/426; 204/421
(58) Field of Search ................................... 204/421–429; 427/126.1, 126.2

(56) References Cited

U.S. PATENT DOCUMENTS

| | | | | |
|---|---|---|---|---|
| 4,715,944 | * | 12/1987 | Yanagida et al. | 204/426 |
| 5,194,134 | * | 3/1993 | Futata et al. | 204/426 |
| 5,755,940 | * | 5/1998 | Shindo | 204/426 |
| 5,993,624 | * | 11/1999 | Matsubara et al. | 204/421 |

* cited by examiner

Primary Examiner—T. Tung
(74) Attorney, Agent, or Firm—Morgan, Lewis & Bockius LLP

(57) ABSTRACT

In a gas sensor element, an alkali metal ion conductor is provided with a detection electrode comprising an alkali metal carbonate in dissociation equilibrium with $CO_2$ gas on one side thereof and a solid standard electrode on the other side thereof. The alkali metal carbonate is bonded to the alkali metal ion conductor via a bonding agent comprising an alkaline earth metal carbonate which is capable of forming an eutectic low-melting composition with the alkali metal carbonate.

11 Claims, 2 Drawing Sheets

GAS SENSOR ELEMENT

BACKGROUND OF THE INVENTION

1. Field of the Invention

This invention relates to a compact and high-sensitivity gas sensor element for measuring chiefly a $CO_2$ concentration in a gas phase and, in addition, $NO_x$, and $SO_x$ concentrations. More particularly, it relates to a gas sensor element in which parts are joined not by mechanical pressing with the aid of bolts, etc. but by contact or bonding using a bonding agent to make the sensor element more compact and more sensitive in detecting gas concentrations. The gas sensor element of the invention ultimately achieves reduction in size and cost and increase in sensitivity of measuring instruments.

The present application is based on Japanese Patent Application No. Hei. 10-80684, which is incorporated herein by reference.

2. Description of the Related Art

In recent years gas sensors capable of measuring mainly a $CO_2$ concentration and secondarily $NO_x$ and $SO_x$ in a gas phase have been developed to cope with the environmental pollution. Of these gas sensors, $CO_2$ sensors are useful for conditioning control in a limited space, such as the space in a vehicle, a house or an office, or for $CO_2$ detection and control in horticultural facilities, and $NO_x$ or $SO_x$ sensors are indispensable to environmental conservation against air pollution.

In these fields, various gas sensors of concentration cell type have recently been proposed, which comprise an alkali metal ion conductor having on each ends thereof a detecting pole, electrodes, etc. However, they have insufficient durability due to deterioration by reactions among constituting materials.

The inventors of the present invention previously proposed a compact and simple gas sensor utilizing an equilibrium reaction which is made of a lithium ion conductor (alkali metal ion conductor), e.g., LISICON, having provided on one side thereof a detection electrode mainly comprising lithium carbonate (alkali metal carbonate) in dissociation equilibrium with $CO_2$ gas and on the other side thereof a solid standard electrode comprising lithium-containing complex oxides different in composition, for example $LiFeO_2$ and $LiFe_5O_8$. A $CO_2$ gas sensor of this type is capable of precisely measuring the $CO_2$ gas concentration in the surrounding atmosphere without using a standard gas.

In order to obtain a practical measuring efficiency with the above $CO_2$ gas sensor, the alkali metal carbonate (detection electrode) in dissociation equilibrium with $CO_2$ gas and the alkali metal ion conductor must be bonded with high strength while securing ion conduction, heat resistance (300° C. or higher), and capability of absorbing the difference in thermal expansion coefficient between them. A mechanical bonding means such as bolts and nuts is conceivable but difficult because the $CO_2$ gas sensor itself is as small as several millimeters. Besides, such a mechanical means would be a bar to size reduction of the sensor. The alkali metal carbonate and the alkali metal ion conductor could be bonded thermally, but such bonding requires heating at a considerably high temperature for a long time. In using, for example, lithium carbonate as an alkali metal carbonate, it melts on heating at temperatures above its melting point (720° C.), resulting in complete disappearance of voids in the detection electrode that are essential to gas diffusion. Further, such heating induces a reaction between lithium carbonate and the alkali metal ion conductor, e.g., LISICON, to form a high-concentration lithium layer in the interface therebetween, which causes a drift of the electromotive force. Correction of such a drift requires a very long time of initial annealing.

SUMMARY OF THE INVENTION

An object of the present invention is to provide a gas sensor element in which an alkali metal carbonate (detection electrode) and an alkali metal ion conductor are bonded in a state as ideal as possible.

The above object is accomplished by previously forming a thin layer containing an appropriate amount of an alkaline earth metal carbonate capable of forming an eutectic low-melting composition with the alkali metal carbonate on the alkali metal ion conductor by coating or a like means, putting a separately prepared alkali metal carbonate plate (detection electrode) on the thin layer, and heating the structure while applying a load thereon to form a molten phase at a low temperature thereby bonding them in a short time.

According to the present invention, since the alkali metal carbonate and the alkali metal ion conductor can be bonded in a short time via a molten phase formed at a low temperature, high electric conductivity can be retained with a reduced initial drift of the electromotive force as long as the composition of the solidified layer of the intermediate eutectic molten phase falls within a certain range.

According to a first aspect of the invention, there is provided a gas sensor element comprising an alkali metal ion conductor, a detection electrode comprising an alkali metal carbonate in dissociation equilibrium with $CO_2$ gas, the detection electrode being provided on a first side of the alkali metal ion conductor, and a solid reference electrode provided on a second side of the alkali metal ion conductor. Further, the detection electrode is bonded to the alkali metal ion conductor via a bonding agent comprising an alkaline earth metal carbonate capable of forming an eutectic low-melting composition with the alkali metal carbonate of the detection electrode.

According to a second aspect of the invention, there is provided a gas sensor element comprising an alkali metal ion conductor, a detection electrode comprising an alkali metal carbonate in dissociation equilibrium with $CO_2$ gas, the detection electrode being provided on one side of the alkali metal ion conductor, and a solid reference electrode provided on the same side on which the detection electrode is provided of the alkali metal ion conductor. The detection electrode is bonded to the alkali metal ion conductor via the bonding agent as aforementioned.

Features and advantages of the invention will be evident from the following detailed description of the preferred embodiments described in conjunction with the attached drawings.

DETAILED DESCRIPTION OF THE PREFERRED EMBODIMENTS

The practice of the present invention will be described by referring to the accompanying drawings.

Figure 1:
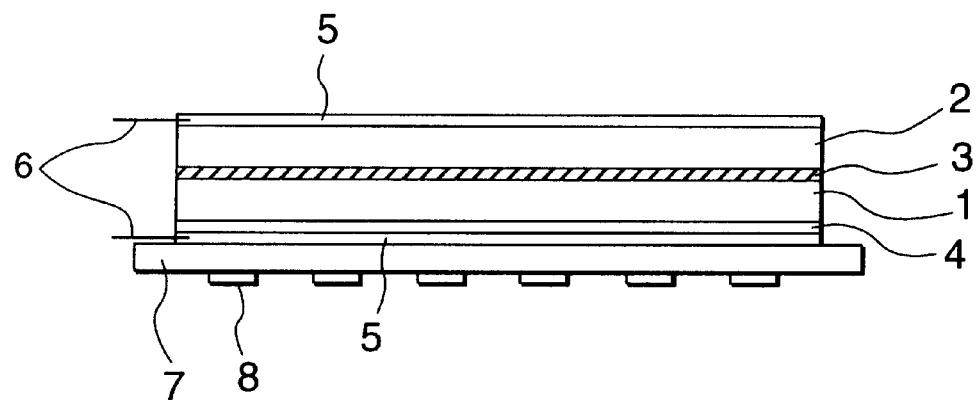
FIG. 1 is a cross-sectional view of the gas sensor element according to an embodiment of the invention.

FIG. 1 shows a cross-sectional view of the gas sensor element according to a first embodiment of the present invention. The gas sensor element shown in FIG. 1 comprises a lithium ion conducting glass plate 1 as an alkali metal ion conductor (alkali metal ion conducting oxide), a lithium carbonate layer (detection electrode) 2 as an alkali metal carbonate in dissociation equilibrium with $CO_2$ gas, a barium carbonate layer 3 (alkaline earth metal carbonate) as a bonding agent for bonding the lithium ion conducting glass plate 1 and the lithium carbonate layer 2, a solid standard electrode 4 made up of a mixture of $LiFeO_2$ and $LiFe_5O_8$, gold paste layers 5, gold lead wires 6, an aluminum substrate 7, and a heater 8.

The gas sensor element having the structure of FIG. 1 can be prepared as follows. A binary equilibrium mixture of $LiFeO_2$ and $LiFe_5O_8$ is applied to one side of a lithium ion conducting glass plate 1 having a prescribed shape and baked to form a solid standard electrode 4. The other side of the glass plate 1 is coated with a thin layer 3 of a mixture comprising an alkali metal carbonate and an alkaline earth metal carbonate capable of forming an eutectic low-melting composition with the alkali metal carbonate at an appropriate mixing ratio. A separately molded alkali metal carbonate layer (detection electrode) 2 having a prescribed shape is placed on the thin layer 3, and heat is applied thereto under a load, whereby a molten phase is formed in low temperature to join the alkali metal carbonate layer 2 to the lithium ion conducting glass plate 1 for a short time. The composition of the solidified layer 3 formed on solidification of the intermediate eutectic molten phase is kept within a certain range so that the resulting gas sensor element has a reduced initial drift in electromotive force and retains high electric conductivity.

Figure 2:
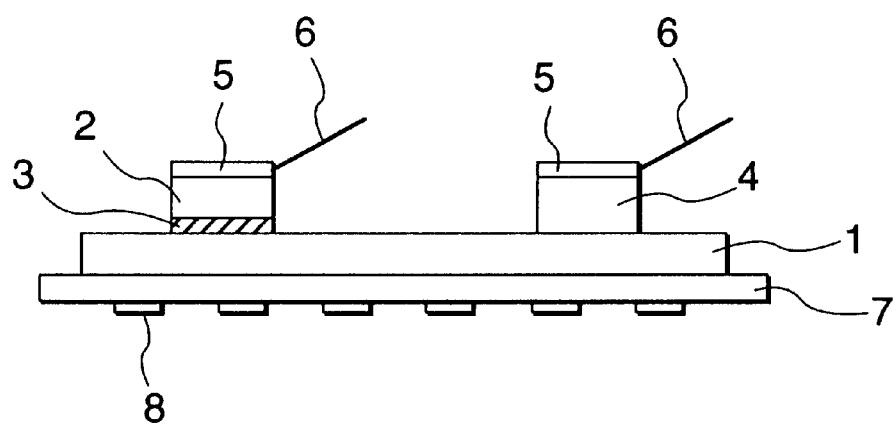
FIG. 2 is a cross-sectional view of the gas sensor element according to a second embodiment of the invention.

FIG. 2 shows a cross-sectional view of the gas sensor element according to a second embodiment of the present invention. The gas sensor element shown in FIG. 2 is composed of a lithium ion conducting glass plate 1 as an alkali metal ion conductor (alkali metal ion conducting oxide), a lithium carbonate layer (detection electrode) 2 as an alkali metal carbonate in dissociation equilibrium with $CO_2$ gas, a barium carbonate layer 3 (alkaline earth metal carbonate) as a bonding agent for bonding the lithium ion conducting glass plate 1 and the lithium carbonate layer 2, a solid standard electrode 4 made up of a mixture of $LiFeO_2$ and $LiFe_5O_8$, gold paste layers 5, gold lead wires 6, an aluminum substrate 7, and a heater 8.

The gas sensor element having the structure of FIG. 2 can be prepared as follows. Lithium carbonate 2 (detection electrode) as an alkali metal carbonate in dissociation equilibrium with $CO_2$ gas is bonded to one end of one side of a lithium ion conducting glass plate 1 using barium carbonate (alkaline earth metal carbonate) as a bonding agent in the same manner as described above. A solid standard electrode 4 made up of a mixture of $LiFeO_2$ and $LiFe_5O_8$ is then directly applied and baked onto the other end of the same side of the lithium ion conducting glass plate 1 apart from the detection electrode 2. A heater 8 is attached to the other side of the lithium ion conducting glass plate 1 via an alumina plate 7. Au lead wires 6 are bonded to the lithium carbonate (detection electrode) 2 and the solid standard electrode 4 via an Au paste 5. The thus prepared gas sensor element has a reduced initial drift in electromotive force and retains high electric conductivity similarly to the first embodiment.

The present invention will now be illustrated in greater detail with reference to Examples in view of Comparative Examples according to conventional techniques.

COMPARATIVE EXAMPLE 1

Bonding of Alkali Metal Ion Conductor and Lithium Carbonate (Detection Electrode) with no Bonding Agent A high-density LISICON plate having a size of 3 mm×3 mm×0.5 mm (t) was used as an alkali metal ion conductor. A binary equilibrium mixture of $LiFeO_2$ and $LiFe_5O_8$ was applied to one side of the plate and baked to form a solid standard electrode. Lithium carbonate powder containing 50 wt % of gold powder was press-molded into a plate (detection electrode) having a size of 3 mm×3 mm×0.5 mm (t), and the plate was put on the other side of the LISICON plate. The resulting 3-layered structure was baked at 700° C. for 10 minutes while applying a load of 10 g uniformly. The detection electrode fell off the LISICON plate in 7 out of 10 samples when the samples were taken out of the furnace and was easily removed with a slight force in the remaining 3 samples.

EXAMPLE 1

An equilibrium binary mixture of $LiFeO_2$ and $LiFe_5O_8$ was applied to one side of the same high-density LISICON plate as used in Comparative Example 1 and baked to form a solid standard electrode.

Figure 3:
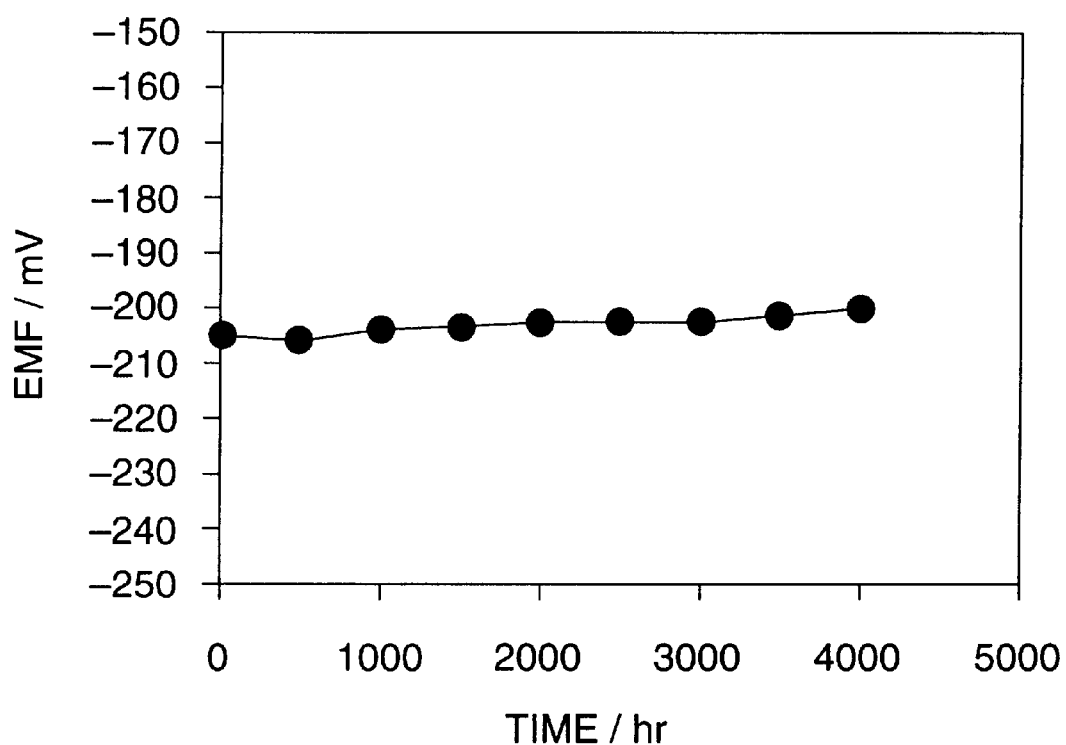
FIG. 3 is a graph of electromotive force of the gas sensor element prepared in Example 1.

A slurry of an equimolar mixture of $Li_2CO_3$ powder (50 mol %) and $BaCO_3$ powder (50 mol %) in ethanol was applied very thinly to the other side of the LISICON plate with a brush and dried. The same Au-containing lithium carbonate plate as used in Comparative Example 1 was put thereon, and the 3-layered structure was baked at 680° C. for 10 minutes under a load of 10 g uniformly applied to form a detection electrode. Five samples were prepared. The detection electrode was found firmly bonded to the LISICON plate in all the 5 samples. Gold paste was applied and baked on the detection electrode and the solid standard electrode to form the respective electrode terminals, and a piece of gold wire was bonded to each terminal by baking with gold paste to provide a lead wire. The electromotive force (EMF) of the resulting gas sensor element was measured at 500° C. in a $CO_2$ gas containing 21 vol % of $N_2$ and 0.1 vol % of $O_2$. The results obtained are shown in FIG. 3. It is apparent from FIG. 3 that the detection electrode is firmly bonded to the high-density LISICON plate.

COMPARATIVE EXAMPLE 2

If the bonding of the electrode is conducted by merely heating the layered structure without applying a load, it is difficult to obtain enough bonding effect. In the comparative example 2, five gas sensor elements were prepared in the same manner as in Example 1, except that the bonding of the detection electrode to the LISICON plate via the slurry of $Li_2CO_3$ and $BaCO_3$ was conducted by heating the 3-layered structure at 680° C. for 10 minutes without applying a load. In all the resulting 5 samples, the detection electrode was seemingly bonded but with a small bonding area. It easily came off by a slight force.

EXAMPLE 2

Five gas sensor elements were prepared in the same manner as in Example 1, except for using a slurry of $BaCO_3$ powder in ethanol as a bonding agent in place of the slurry of $Li_2CO_3$ and $BaCO_3$. All the resulting samples showed strong adhesion of the detection electrode to the glass plate. A gold electrode terminal and a gold lead wire were attached to each electrode in the same manner as in Example 1. The electromotive force of the resulting gas sensor element was measured at 500° C. in a $CO_2$ gas containing 21 vol % of $N_2$ and 0.1 vol % of $O_2$. The initial electromotive force was 300 mV, showing a considerable drift from the theoretical value, requiring 15 days before the theoretical electromotive force was reached. However, there was no problem for a practical use.

In the above Examples, if LISICON having a low relative density and metal carbonate having a low relative density are used, lithium ions and electrons are hardly transported, resulting in reduction of the electromotive force generated by the detection electrode reaction below the theoretical value. The reduction of the generated power with decreasing relative densities of LISICON and metal carbonate is shown in the following table, in which the theoretical electromotive force is taken as 1.

| Relative Density (%) | 85 | 90 | 95 | 97 |
|---|---|---|---|---|
| EMF Index | 0.8 | 0.82 | 0.96 | 0.99 |

Therefore, LISICON having a relative density of 95% or higher and a metal carbonate having a relative density of 95% or higher were used in the present invention to minimize the reduction in electromotive force. Use of such dense LISICON and metal carbonate not only brings about improved ion conductivity but excludes influences of other gases thereby to secure the electromotive force stability of the $CO_2$ gas sensor.

According to the present invention, it was proved very effective to use a low-melting composition eutectic with an alkali metal carbonate, e.g., lithium carbonate, as a bonding agent in bonding a detection electrode comprising lithium carbonate containing a gold powder to the surface of a high-density LISICON plate. Use of the low-melting composition makes it possible to complete the bonding operation at a relatively low temperature in a short time. As a result, an undesired reaction between LISICON and lithium carbonate can be suppressed, which reaction may produce a large amount of a reaction product forming an electrically insulating layer in the interface.

A metal carbonate in dissociation equilibrium with $CO_2$ gas (detection electrode) and an alkali metal ion conducting oxide can be firmly joined together with barium carbonate (alkaline earth metal carbonate) as a bonding material. Barium carbonate secures ion conductivity and heat resistance while absorbing the difference in thermal expansion coefficient between the metal carbonate and the alkali metal ion conducting oxide. Therefore, a gas sensor can be made up of a fewer parts without sacrificing the sensor function, making it possible to reduce the size and to improve sensitivity. This will lead to achievement in reduction in size and cost and improvement in precision of measuring instruments.

Where dense LISICON (alkali metal ion conductor) and a dense metal carbonate are used, the electromotive force stability of the $CO_2$ gas sensor can be secured, leading to increased precision in detecting a $CO_2$ gas concentration.

Although the invention has been described in its preferred form with a certain degree of particularity, it is understood that the present disclosure of the preferred form can be changed in the details of construction and in the combination and arrangement of parts without departing from the spirit and the scope of the invention as hereinafter claimed.

What is claimed is:

1. A gas sensor element comprising:
   an alkali metal ion conductor;
   a detection electrode comprising an alkali metal carbonate in dissociation equilibrium with $CO_2$ gas, said detection electrode being provided on a first side of said alkali metal ion conductor;
   a solid reference electrode provided on a second side of said alkali metal ion conductor; and
   a bonding agent, for bonding said detection electrode comprising the alkali metal carbonate to said alkali metal ion conductor, provided between said detection electrode and said alkali metal ion conductor, said bonding agent comprising an alkaline earth metal carbonate capable of forming an eutectic low-melting composition with the alkali metal carbonate of said detection electrode.

2. A gas sensor element according to claim 1, wherein said bonding agent comprises one of a mixture and a solid solution comprising said alkaline earth metal carbonate and an alkali metal carbonate in dissociation equilibrium with $CO_2$ gas.

3. A gas sensor element according to claim 2, wherein said bonding agent contains 50 mol % of the alkaline earth metal carbonate.

4. A gas sensor element according to claim 3, wherein said bonding agent is bonded to said alkali metal ion conductor by melting said bonding agent at or above a fluidizing temperature of said alkali metal carbonate in dissociation equilibrium with $CO_2$ gas.

5. A gas sensor element according to claim 1, wherein said alkali metal ion conductor and said metal carbonates have a relative density of 95% or higher.

6. A gas sensor element comprising:
   an alkali metal ion conductor;
   a detection electrode comprising an alkali metal carbonate in dissociation equilibrium with $CO_2$ gas, said detection electrode being provided on one side of said alkali metal ion conductor;
   a solid reference electrode provided on said one side of said alkali metal ion conductor; and
   a bonding agent for bonding said detection electrode comprising the alkali metal carbonate to said alkali metal ion conductor, said bonding agent comprising an alkaline earth metal carbonate capable of forming an eutectic low-melting composition with the alkali metal carbonate of said detection electrode.

7. A gas sensor element according to claim 6, wherein said bonding agent comprises one of a mixture and a solid solution comprising said alkaline earth metal carbonate and an alkali metal carbonate in dissociation equilibrium with $CO_2$ gas.

8. A gas sensor element according to claim 7, wherein said bonding agent contains 50 mol % of the alkaline earth metal carbonate.

9. A gas sensor element according to claim 8, wherein said bonding agent is bonded to said alkali metal ion conductor by melting said bonding agent at or above a fluidizing temperature of said alkali metal carbonate in dissociation equilibrium with $CO_2$ gas.

10. A gas sensor element according to claim 6, wherein said alkali metal ion conductor and said metal carbonates have a relative density of 95% or higher.

11. A method of manufacturing a gas sensor element comprising the steps of:
   forming an alkali metal ion conductor;
   forming a bonding layer on the alkali metal ion conductor; and
   forming a detection electrode by placing a separately molded layer comprising an alkali metal carbonate on the bonding layer, wherein the bonding layer comprises an alkaline earth metal carbonate capable of forming an eutectic low-melting composition with said alkali metal carbonate of said detection electrode.

* * * * *